United States Patent [19]

Hsu

[11] 4,200,580
[45] Apr. 29, 1980

[54] DIOXANYLPHENYL BENZOATE LIQUID CRYSTAL COMPOUNDS

[75] Inventor: Ying Y. Hsu, Bridgewater, N.J.

[73] Assignee: Timex Corporation, Waterbury, Conn.

[21] Appl. No.: 17,634

[22] Filed: Mar. 5, 1979

[51] Int. Cl.² ........................................ C07D 319/04
[52] U.S. Cl. .................. 260/340.7; 340/784; 260/463; 260/465 D; 560/20; 560/61; 560/66; 568/864
[58] Field of Search ..................................... 260/340.7

[56] References Cited
PUBLICATIONS

Chem. Abstracts, 66: 115184t, (1967–1971 Subject Index 4205s).

Chem. Abstracts 78: p44931u, (1972–1976 Chem. Substance Index 6497cs).

Primary Examiner—Ethel G. Love
Attorney, Agent, or Firm—Edward J. Timmer

[57] ABSTRACT

Compounds of the formula:

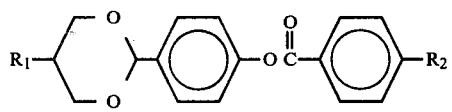

wherein $R_1$ is a straight chain alkyl group of 1 to 10 carbon atoms and $R_2$ is an alkyl, alkoxy, acyloxy, alkyl carbonato group having 1 to 10 carbon atoms, CN or $NO_2$. The dioxanylphenyl benzoate compounds of the invention are useful as liquid crystal materials in electro-optical displays.

3 Claims, No Drawings

DIOXANYLPHENYL BENZOATE LIQUID CRYSTAL COMPOUNDS

BACKGROUND OF THE INVENTION

It is known to use nematic liquid crystal compounds in electrooptic displays. Such displays are utilized in constantly increasing numbers in watches and other instruments. Such devices are well known to those skilled in the art.

One of the problems encountered in the utilization of nematic liquid crystal materials in such displays is the availability of stable low viscosity nematic compounds which are liquid at near room temperatures and have relatively low transition temperatures to make them practical for use in electro-optic display devices. Further, it is desirable that the nematic liquid crystal material require the application of the minimal amount of potential to obtain the desired effect in order to minimize the power requirements in the display device. Only an extremely limited number of nematic liquid crystal compounds thus far known posses these desired characteristics.

One compound possessing the aforementioned combination of properties is described more fully in copending U.S. patent application Ser. No. 17,635 filed Mar. 5, 1979 entitled "5-Alkyl-2-(4-Cyanophenyl)-1,3-Dioxanes" in the name of Howard Sorkin as inventor and of common assignee herewith. The compound of that patent application is represented by the formula:

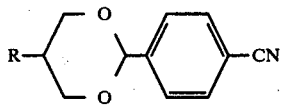

where R is an alkyl of 1 to 8 carbon atoms. As a result of their somewhat limited nematic range, these compounds are preferably mixed with other liquid crystal materials in order to formulate liquid crystal mixtures with a wide nematic temperature range.

SUMMARY OF THE INVENTION

According to the present invention there is provided a new group of compounds which are stable liquid crystal materials having a dioxane moiety in aromatic ester molecules. Such compounds are useful as components in formulating liquid crystal mixtures with the aforementioned cyanophenyl dioxane compounds or other types of liquid crystal materials.

The compounds of the present invention are of the formula:

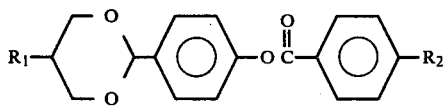

wherein $R_1$ is an alkyl group of 1 to 10 carbon atoms and $R_2$ is an alkyl, alkoxy, acyloxy, akyl carbonato group having 1 to 10 carbon atoms, CN or $NO_2$.

The dioxanylphenyl benzoate compounds of the above formula represent a new class of liquid crystal materials which are useful as components of liquid crystal mixtures in electro-optical displays.

The compounds of the present invention may be prepared by at least two methods:

METHOD I

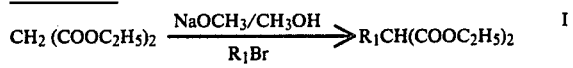

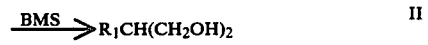

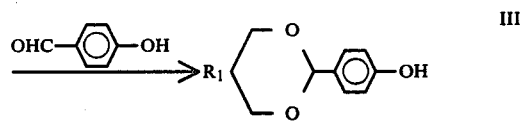

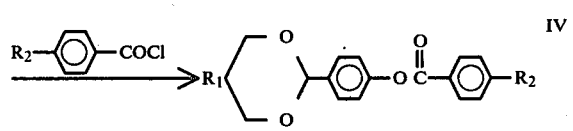

METHOD II

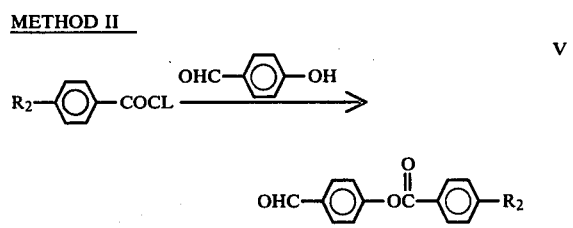

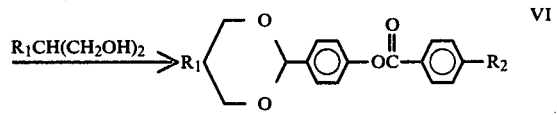

In the foregoing synthesis $R_1$ and $R_2$ have the same meaning as previously indicated.

The dioxanylphenyl benzoates of the present invention are obtained as two isomers. Since the trans configuration is elongated, it presumably is the one which accounts for liquid crystalline characteristics of the compounds.

The nature of the invention may be better understood by the following representative embodiments which are included to illustrate the nature of the invention without limiting its scope which is defined in the claims.

SPECIFIC EMBODIMENTS

EXAMPLE 1

Preparation of p-(5-n-octyl-1,3-dioxan-2-yl)phenyl p-n-butylbenzoate

According to Method I

Diethyl-n-octylmalonate—Step I where $R_1=C_8H_{17}$ n-Octylbromide (193 g, 1 m) was slowly added to a mixture of 25% sodium methoxide solution (216 g, 1 m), diethyl malonate (160 g, 1 m) and methanol (1 l) with stirring at room temperature. The resulting mixture was refluxed until neutral to litmus (about 24 hours). The solvent was stripped off and the residue was filtered and washed with chloroform. The filtrate was evaporated to remove chloroform and the residue was vacuum-distilled to yield diethyl n-octylmalonate (180 g, 66%) bp 105°–115° C./0.5–0.7 mm.

2-n-Octylpropane-1,3 diol—step II where $R_1=C_8H_{17}$

Borane methyl sulfide (BMS) complex (80 g, 1 m) was added dropwise to a mixture of diethyl-n-octylmalonate (90 g, 0.33) and tolune (400 ml) with stirring at room temperature. Stirring was continued for an additional hour. The mixture was refluxed gently for 10 hours, cooled to 20° C., and then poured slowly into ice-cold methanol (400 ml) with stirring and left to stand overnight. The solvent was stripped off and the residue was stirred with 10% hydrochloric acid solution (400 ml) overnight. The resulting mixture was extracted with chloroform (2×70 ml) and washed with water until neutral to litmus. The solvent was evaporated and the residue was vacuum distilled to yield 2-n-octylpropane-1,3-diol (25.5 g, 41%) bp 135°–140° C./0.5–0.8 mm.

p-(5-n-Octyl-1,3-dioxan-2-yl)phenol—Step III where $R_1=C_8H_{17}$

A mixture of 2-n-octylpropane-1,3-diol (5.64 g, 0.03 m), 4-hydroxybenzaldehyde (3.66 g, 0.03 m), benzene (60 ml) and a catalytic amount of 4-toluenesulfonic acid was azeotropically refluxed until no more water was collected (about 16 hours). The solvent was evaporated and the residue was crystallized from 50% aqueous ethanol to yield p-(5-n-octyl-1,3-dioxan-2-yl)phenol (4 g, 48%) mp 96°–97° C.

p-(5-n-Octyl-1,3-dioxan-2-yl)phenyl p-n-butylbenzoate—Step IV where $R_1=C_8H_{17}$ and $R_2=C_4H_9$ A mixture of 4-n-butylbenzoyl chloride (0.98 g. 0.005 m), p-(5-n-octyl-1,3-dioxan-2-yl)phenol (1.37 g, 0.005 m), benzene (40 ml) and pyridine (2 ml) was stirred at room temperature for six hours. The resulting reaction mixture was poured into cold water. The organic layer was separated and washed with diluted hydrochloric acid solution, diluted potassium hydroxide solution and water, then dried over anhydrous sodium sulfate. The solvent was evaporated and the residue was crystallized from ethanol to yield p-(5-n-octyl-1,3-dioxan-2-yl)phenyl p-n-butylbenzoate (1.1 g. 51%) CN 65.5°–66.5° C., NL 141°–142° C.

EXAMPLE 2

Preparation of p-(5-n-butyl-1,3-dioxan-2-yl)phenyl p-n-butylbenzoate

According to Method II p-(4'-n-Butylbenzoyloxy)benzaldehyde—Step V where $R_2=C_4H_9$ 4-n-Butylbenzoyl chloride (39, 2 g, 0.2 m) was added dropwise to a solution of 4-hydroxybenzaldehyde (24.4 g), (0.2 m) anhydrous benzene (320 ml) and dry pyridine (30 ml) with stirring. After completion of addition stirring was continued for 24 hours at room temperature. The resulting reaction mixture was poured into cold water. The organic layer was separated and washed with diluted hydrochloric acid solution, diluted potassium hydroxide solution and water, then dried over anhydrous sodium sulfate. The solvent was evaporated and the residue was crystallized from ethanol to yield p-(4'-n-butylbenzoyloxy)benzaldehyde (26.3 g, 46%) mp 49.7° C.

p-(5-n-Butyl-1,3-dioxan-2-yl)phenyl p-n-butylbenzoate—Step VI where $R_1=R_2=C_4H_9$ A mixture of 2-n-butylpropane-1,3-diol (6.6 g, 0.05 m) and p-(4'-n-butylbenzoyloxy)benzaldehyde (14.2 g, 0.05 m), benzene (100 ml) and a catalytic amount of 4-toluenesulfonic acid was azeotropically refluxed until no more water was collected. The solvent was evaporated and the residue was crystallized from ethanol to yield p-(5-n-butyl-1,3-dioxan-2-yl)phenyl p-n-butylbenzoate (13.4 g 67%) CN 79.2°–80.2° C., NL 160° C.

Additional examples of the p-(5-n-alkyl-1,3-dioxan-2-yl)phenyl p-substituted, along with their transition temperatures, are given in Table I.

TABLE I

Phase transition temperatures for p-(5-n-alkyl-1,3-dioxan-2-yl) phenyl p-substituted benzoates:

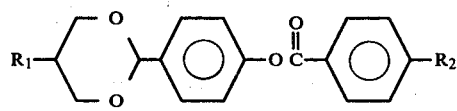

| Compound | $R_1$ | $R_2$ | $C_1C$ (CS) | CN (SN) | NL |
|---|---|---|---|---|---|
| 1 | $C_4H_9$ | $CH_3$ | | 117–118 | 180 |
| 2 | $C_4H_9$ | $C_4H_9$ | | 79–80 | 160 |
| 3 | $C_4H_9$ | $C_5H_{11}$ | | 83.8–85 | 153 |
| 4 | $C_4H_9$ | $C_6H_{13}$ | | 72.1–73 | 148 |
| 5 | $C_4H_9$ | $C_7H_{15}$ | | 87.4–88.4 | 146.2 |
| 6 | $C_5H_{11}$ | $C_3H_7$ | | 101.5–102.5 | 174 |
| 7 | $C_5H_{11}$ | $C_4H_9$ | | 92–93 | 133.5 |
| 8 | $C_5H_{11}$ | $C_5H_{11}$ | | 103.5–104.5 | 154.6 |
| 9 | $C_6H_{13}$ | $C_4H_9$ | | 80–81.5 | 150 |
| 10 | $C_6H_{13}$ | $C_5H_{11}$ | | 76.5–77.5 | 114.5 |
| 11 | $C_6H_{13}$ | $C_6H_{13}$ | | 88.2–89.2 | 147 |
| 12 | $C_6H_{13}$ | $C_7H_{15}$ | | 87.8–88.2 | 147.6 |
| 13 | $C_7H_{15}$ | $C_3H_7$ | 82–83 | 92–93 | 152.5 |
| 14 | $C_7H_{15}$ | $C_4H_9$ | 44–45 | 65.5–66 | 131 |
| 15 | $C_7H_{15}$ | $C_5H_{11}$ | 48–49 | 71.5–72.5 | 125.2 |
| 16 | $C_8H_{17}$ | $C_3H_7$ | 73.5–74.5 | 88.2–89.2 | 141.4 |
| 17 | $C_8H_{17}$ | $C_4H_9$ | | 65.5–66.5 | 141.5 |
| 18* | $C_8H_{17}$ | $C_5H_{11}$ | (59.5–60.5) | (64.2–65.2) | 146.5 |
| 19 | $C_8H_{17}$ | $C_6H_{13}$ | | (71) | 133.5 |
| 20 | $C_8H_{17}$ | $C_7H_{15}$ | (62.5) | (71.2) | 130 |
| 21 | $C_6H_{13}$ | CN | (134–135) | (170) | 232 |

*Compounds 13 through 16 exhibit additional crystal to crystal transition and compounds 17 through 20 exhibit monotropic smectic polymorphism.

While the invention has been explained by a detailed description of certain specific embodiments, it is understood that various modifications and substitutions can be made in any of them within the scope of the appended claims which are intended to include equivalents of such embodiments.

What is claimed is:

1. A compound of the formula:

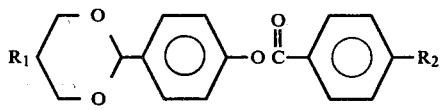

wherein $R_1$ is an alkyl group having 1 to 10 carbon atoms and $R_2$ is an alkyl, alkoxy, acyloxy, alkyl carbonato group having 1 to 10 carbon atoms, CN or $NO_2$.

2. A compound as claimed in claim 1 wherein $R_1$ is a straight chain alkyl.

3. A liquid crystal material of the formula:

wherein $R_1$ is a straight chain alkyl group having 1 to 10 carbon atoms and $R_2$ is an alkyl, alkoxy, acyloxy, alkyl carbonato group having 1 to 10 carbon atoms, CN or $NO_2$.

* * * * *